(12) United States Patent
Bertola

(10) Patent No.: US 6,248,902 B1
(45) Date of Patent: Jun. 19, 2001

(54) PROCESS FOR THE PRODUCTION OF N-METHYL PYRROLIDONE

(75) Inventor: Aldo Bertola, Milan (BE)

(73) Assignee: Pantochim S. A., Feluy (BE)

( * ) Notice: Subject to any disclaimer, the term of this patent is extended or adjusted under 35 U.S.C. 154(b) by 0 days.

(21) Appl. No.: 09/445,509

(22) PCT Filed: Apr. 2, 1999

(86) PCT No.: PCT/EP99/02296

§ 371 Date: Feb. 4, 2000

§ 102(e) Date: Feb. 4, 2000

(87) PCT Pub. No.: WO99/52867

PCT Pub. Date: Oct. 21, 1999

(30) Foreign Application Priority Data

Apr. 9, 1998 (BE) .................................................. 9800274

(51) Int. Cl.$^7$ .................. C07D 207/263; C07D 207/267
(52) U.S. Cl. ........................................... 548/541; 548/552
(58) Field of Search ..................... 548/552, 541

(56) References Cited

U.S. PATENT DOCUMENTS

| 3,775,431 | 11/1973 | Rodewald . | |
|---|---|---|---|
| 6,008,375 | * 12/1999 | Bergfeld et al. | 548/554 |

FOREIGN PATENT DOCUMENTS

| 2159859 | 7/1972 | (DE) . |
|---|---|---|
| 4203527 | 8/1993 | (DE) . |

OTHER PUBLICATIONS

Chemical Abstracts, vol. 124, No. 11, Mar. 11, 1996, Yang, Yuanyi et al, "Improved process for producing N–methylpyrrolidone and 2–pyrrolidone".

Chemical Abstracts, vol. 43, No. 11, Jun. 10, 1949, McElvain et al, "Piperidine Derivatives. XX. The preparation and Reactions of 1–methyl–3–piperidone".

Chemical Abstracts, vol. 31, No. 7, Apr. 10, 1937, Spath et al, "Formation of lactams from lactones".

Abstract of JP 7221420, Aug. 18, 1995.

Albrecht Ludwig Harreus, Ullman's Encyclopedia of Industrial Chemisty, 5$^{th}$ revised edition, vol. A22, pp. 457–459, 1993.*

* cited by examiner

Primary Examiner—Joseph K. McKane
Assistant Examiner—Sonya Wright
(74) Attorney, Agent, or Firm—Stevens, Davis, Miller & Mosher, LLP

(57) ABSTRACT

A process for the production of N-methyl-pyrrolidone obtained by reaction of gammabutyrolactone and mononmethylamine; wherein the synthesis is carried out by a continuous non catalytic process in liquid phase, via three distinct reaction stages connected in series.

13 Claims, 1 Drawing Sheet

PROCESS FOR THE PRODUCTION OF N-METHYL PYRROLIDONE

This application is a 371 of PCT/EP99/02296 filed Apr. 2, 1999.

The present invention relates to the production of N-methyl pyrrolidone. In particular, it relates to the use of gamma-butyrolactone and monomethylamine as starting materials for that purpose, by a continuous process, in such a way that the product is obtained in optimal purity and yields.

It is known from the prior art that there exist several processes for the synthesis of N-methyl pyrrolidone (NMP) with gamma butyrolactone (GBL) and monomethylamine (MMA) as starting materials.

In J.Am.Chem.Soc., March 1949, pag. 897, Elvain and Vozza described a synthetic strategy aimed at the production of NMP with GBL and MMA as starting materials that exploited a discontinuous process, and with a double amount of the latter two in comparison with their stoichiometric values.

After 4 hours of reaction at 280° C., NMP was recovered by distillation with a 90–93% yield.

In 1936 Spath and Lunder (Berichte 69, pag 2727) described a similar process wherein a large excess of methylamine (4 mols per mol of GBL) was fed to a discontinuous reactor, with an approximately 90% conversion after 3 hours.

NMP product purification involved complex dissolution processes, to be carried out in the ether from the effluent of the reaction and the ensuing distillations.

In several patents (JP 7 221 420; JP 7400259; JP 7 420 585; JP 7 642 107) Mitsubishi Chemical industries Co. Ltd. of Japan described continuous processes for the synthesis of NMP using GBL and MMA as starting materials. These are characterised by reactions with high molar ratios between water and shot GBL (typically ranging between 3 and 4 mols of water for each mol of GBL) and by the presence of great amounts of MMA (typically with molar ratios ranging between 1.4 and 3 mols of MMA per mol of GBL).

The processes designed by Mitsubishi result to be disadvantaged in terms of the high costs involved with the separation of unreacted MMA and its recovery and with the separation of the water forwarded to the reaction to which synthesis water adds up (one mol of water for each mol of reacted GBL).

To avoid the drawbacks associated with the discontinuous reaction in the presence of excess MMA and water, alternative methodologies have been proposed and these are based on the employment of catalysts.

In German Patent n° 2,159,858 owned by Mobil Oil a synthesis with GBL, MMA in the presence of 13X type zeolites is described.

In German Patent 4,203,527 owned by AKZO, a synthesis involving GEL, MMA and steam in the gas phase and at a temperature of 275° C., on an NaX type zeolite is described.

The above processes did not succeed in being applied industrially, as the employment of a catalyst subject to regenerations is disadvantageous in terms of the economic balance of the process as compared with non catalytic processes.

A first aim of the present invention is that of proposing a process wherein no catalysts are employed and thanks to which a high percentage of MMA and GBL is converted with high selectivities. The above features give way to the production of NMP at low investment costs and raw material and utility consumption.

Another aim of the present invention is to get the reaction to take place in a continuous fashion, without feeding any water, and with low molar ratios between shot MMA and GBL.

The above aims were accomplished by the employment of a process for the production of N-methyl-pyrrolidone obtained by reaction of gamma butyrolactone and monomethylamine, characterised in that the synthesis is carried out by a continuous non catalytic process in the liquid phase, via three distinct reaction stages connected in series.

These and other features will be more readily apparent from the following description of a preferred not limiting embodiment of the invention with reference to the accompanying drawings in which the process scheme is shown.

According to the present invention the three stages of the reaction are characterised by what follows:

| I stage of reaction | |
|---|---|
| MMA:GBL molar ratio | =between 1.05 and 1.4 |
| Temperature (reactor outlet) | =between 150 and 220° C. |
| Residence time | =between 5 and 30 minutes |
| II stage of reaction | |
| Temperature | =between 220 and 270° C. |
| Residence time | =between 1 and 3 hours |
| III stage of reaction | |
| Temperature | =between 250 and 310° C. |
| Residence time | =between 0.5 and 2.0 hrs |

In the three reactors pressure ranges between 30 and 90 ATE, so as to keep the reactants in their liquid phase. An ATE is a Technical Atmosphere. One Technical Atmosphere equals 1.103 bar, thus 30 ATE equals 30.39 barg and 90 ATE equals 91.17 barg.

In the three reaction stages, all reactors are of the adiabatic type and preferably tubular in shape.

Adequate reactors are also vessels subdivided into compartments by means of separation septs that avoid the reaction products to mix again as the reaction progresses.

In the first reactor GBL exothermally reacts with MMA to afford N-methyl-hydroxylbutyramide (NMH).

In the following reactor an NMH cyclisation reaction is triggered with formation of water and NMP.

In the final stage, the NMP formation reaction goes to completion at high temperature.

The succession of the three subsequent reaction stages as they are described in the present process leads to a reduction in GBL and NMP contents in the reaction effluents, which is a necessary condition for producing high purity NMH (99.5% minimum weight).

GBL, whose boiling point at STM is very close to that of NMP (202° C.) could not be separated from NMP by distillation.

BRIEF DESCRIPTION OF DRAWINGS

A scheme of the reaction process is shown in the attached drawing.

During distillation, NMH would tend to go off again yielding MMA and GBL that would contaminate the product because not separable.

Figure 1:
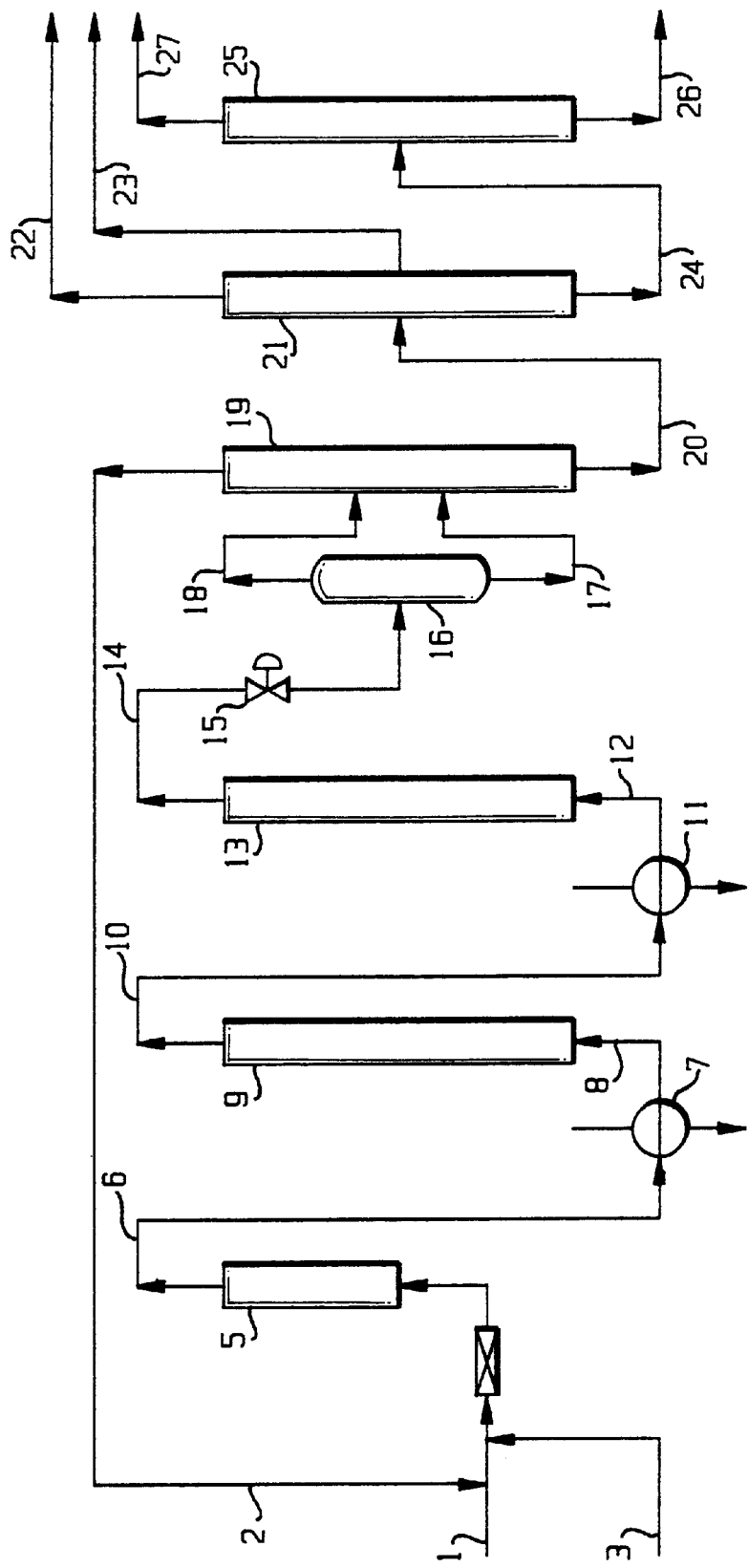

MMA in the shot (line 1) together with that in the recycle (line 2) mixes with shot GBL (line 3) in static mixer 4 with a molar ratio of 1.2:1 between MMA and GBL.

The mixing activates the addition reaction with formation of NMH.

This reaction is strongly exothermal and once gone to completion it takes the mass temperature up to about 190° C.

The addition reaction goes to completion in reactor 5 within about 15 minutes.

The liquid stream from the reactor (line 6) is heated up further in exchanger 7, by means of hot oil, and its temperature is taken up to 250° C.

After preheating, the liquid (line 8) feeds reactor 9 where NMH starts to cyclise, while water forms at the same time.

Residence time in reactor 9 is approximately 2 hrs.

The reactor is of the tubular type, otherwise it is a vessel subdivided into compartments by separation septs that have the function of keeping the reaction products from mixing again.

The effluents from reactor 9 (line 10) feed heater 11 where temperature is raised to 280° C. by thermal exchange with hot oil.

After the second preheating, the liquid (line 12) feeds reactor 13 where conversion of NMH to NMP goes to completion with an approx. 1.5 hr. residence time.

The effluent from reactor 13 (line 14) has the following typical molar composition:

| | |
|---|---|
| NMP | 43.7% |
| NMH | traces |
| MMA | 9.8% |
| Light Byproducts | 0.7% |
| Heavy Byproducts | 1.0% |
| Water | 44.8% |

Through valve 15, the effluent pressure is reduced down to approximately 9 ATE producing a liquid phase in separator 16 (line 17), and a vapour phase (line 18) which both feed fractionation column 19 where top MMA separates and is recycled to the reaction (line 2).

The bottom product of column 19 feeds (line 20) subsequent column 21, wherein at the top reaction water separates (line 22) while (line 23) light organic byproducts are obtained, too.

The bottom product in column 21 feeds (line 24) fractionation column 25 where at the bottom (line 26) of which heavy by-products whereas at the top (line 27) purified NMP separate.

After GC analysis NMP results to be no less pure than 99.5% by weight, with a water content lower than 0.05 by weight.

What is claimed is:

1. A process for the production of N-methylpyrrolidone obtained by reaction of gamma butyrolactone and monomethylamine, wherein the synthesis is carried out by a continuous non catalytic process in the liquid phase, via a reaction system comprising three distinct reaction stages connected in series, comprising:

a) operating the first stage of the reaction at a temperature ranging between 150° and 220° C. at a first stage reactor outlet, with a residence time ranging between 5 and 30 minutes;

b) operating the second stage of the reaction at a temperature ranging between 220° and 270° C. at a second stage reactor inlet, with a residence time ranging between 1 and 3 hrs; and c) operating the third stage of the reaction at a temperature ranging between 250° and 310° C. at a third stage reactor inlet, with a residence time ranging between 0.5 and 2.0 hrs.

2. A process according to claim 1 wherein the first stage of the reaction operates at temperatures ranging between 170° and 200° C. at the reactor outlet.

3. A process according to claim 1, wherein the first stage of the reaction operates with a residence time ranging between 10 and 15 minutes.

4. A process according to claim 1, wherein at the second stage of the reaction, residence time ranges between 1.5 and 2.5 hours.

5. A process according to claim 1, wherein at the third stage of the reaction residence time ranges between 1.0 and 1.5 hours.

6. A process according to claim 1, wherein shot of the reaction system has a molar ratio of monomethylamine to gammabutyrolactone ranging between 1.05 and 1.4.

7. A process according to claim 6, wherein the molar ratio of monomethylamine to gammabutyrolactone ranges between 1.1 and 1.2.

8. A process according to claim 1, wherein the monomethylamine and gammabutyrolactone are kept in the liquid phase by operating with three reaction stages at pressures ranging between 30 and 90 ATE.

9. A process according to claim 8, wherein the three reaction stages are operated at pressures ranging between 40 and 60 ATE.

10. A process according to claim 1, wherein reactors of each of the three reaction stages comprise vessels comprising septs with the function of creating a piston type reactant flow through separate reaction compartments which keep the products from remixing.

11. A process according to claim 10, wherein the reactors of each of the three reaction stages comprise tubular vessels.

12. A process according to claim 1, wherein reactors of each of the three reaction stages consist of vessels comprising septs with the function of creating a piston type reactant flow through separate reaction compartments which keep the products from remixing.

13. A process according to claim 11, wherein the reactors of each of the three reaction stages consist of tubular vessels.

* * * * *